US00PP23771P2

(12) United States Plant Patent
Kanaya

(10) Patent No.: US PP23,771 P2
(45) Date of Patent: Jul. 23, 2013

(54) CALIBRACHOA PLANT NAMED 'SUNBELKULAVE'

(50) Latin Name: ***Calibrachoa* sp.**
Varietal Denomination: Sunbelkulave

(75) Inventor: Takeshi Kanaya, Saitama (JP)

(73) Assignee: Suntory Flowers Ltd., Tokyo (JP)

( * ) Notice: Subject to any disclaimer, the term of this patent is extended or adjusted under 35 U.S.C. 154(b) by 183 days.

(21) Appl. No.: 13/134,383

(22) Filed: Jun. 6, 2011

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — C. A. Whealy

(57) ABSTRACT

A new and distinct cultivar of *Calibrachoa* plant named 'Sunbelkulave', characterized by its trailing plant habit; vigorous growth habit; freely branching and flowering plant habit; early and long flowering period; large single purple violet-colored flowers with dark purple-colored venation; and good garden performance.

1 Drawing Sheet

Botanical designation: *Calibrachoa* sp.
Cultivar denomination: 'SUNBELKULAVE'.

BACKGROUND OF THE INVENTION

The present invention relates to a new and distinct cultivar of *Calibrachoa* plant, botanically known as *Calibrachoa* sp. and hereinafter referred to by the name 'Sunbelkulave'.

The new *Calibrachoa* plant is a product of a planned breeding program conducted by the Inventor in Higashiomi, Shiga, Japan. The objective of the breeding program is to develop new trailing and freely branching *Calibrachoa* plants with large, attractive and uniquely colored flowers.

The new *Calibrachoa* plant originated from a cross-pollination conducted by the Inventor in Higashiomi, Shiga, Japan in April, 2006 of a proprietary selection of *Calibrachoa* sp. identified as code name CE11, not patented, as the female, or seed, parent with a proprietary selection of *Calibrachoa* sp. identified as code name CP3, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in September, 2007.

Asexual reproduction of the new *Calibrachoa* plant by vegetative cuttings in a controlled greenhouse environment in Higashiomi, Shiga, Japan since November, 2007, has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environment conditions such as temperature and light intensity without, however, any variance in genotype.

The following traits have been repeatedly observed and are determined to be the unique characteristics of 'Sunbelkulave'. These characteristics in combination distinguish 'Sunbelkulave' as a new and distinct *Calibrachoa* plant:

1. Trailing plant habit.
2. Vigorous growth habit.
3. Freely branching and flowering plant habit.
4. Early and long flowering period.
5. Large single purple violet-colored flowers with dark purple-colored venation.
6. Good garden performance.

Plants of the new *Calibrachoa* can be compared to plants of the female parent selection. Plants of the new *Calibrachoa* differ primarily from plants of the female parent selection in plant size and plant habit as plants of the female parent selection are smaller and more outwardly spreading than plants of the new *Calibrachoa*.

Plants of the new *Calibrachoa* can be compared to plants of the male parent selection. Plants of the new *Calibrachoa* differ primarily from plants of the male parent selection in the following characteristics:

1. Leaves of plants of the new *Calibrachoa* are narrower than leaves of plants of the male parent selection.
2. Plants of the new *Calibrachoa* and the male parent selection differ in flower color as plants of the male parent selection have darker purple violet-colored flowers.

Plants of the new *Calibrachoa* can also be compared to plants of 'Sunbelrikubu', disclosed in U.S. Plant Pat. No. 20,505. In side-by-side comparisons conducted in Higashiomi, Shiga, Japan, plants of the new *Calibrachoa* and 'Sunbelrikubu' differed primarily in the following characteristics:

1. Leaves of plants of the new *Calibrachoa* were longer and narrower than leaves of plants of 'Sunbelrikubu'.
2. Plants of the new *Calibrachoa* and 'Sunbelrikubu' differed in flower color as plants of 'Sunbelrikubu' had purple-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbelkulave' grown in a container.

The photograph at the bottom of the sheet is a close-up view of a typical flowering plant of 'Sunbelkulave'.

DETAILED BOTANICAL DESCRIPTION

The aforementioned photographs and following observations, measurements and values describe plants grown during the spring and early summer in 15-cm containers in an outdoor nursery in Higashiomi, Shiga, Japan and under commercial practices. During the production of the plants, day temperatures averaged 23° C. and night temperatures averaged 13° C. Plants were four months old when the photographs and the description were taken. In the following description, color references are made to The Royal Horticultural Society Colour Chart, 2001 Edition, except where general terms of ordinary dictionary significance are used.

Botanical classification: *Calibrachoa* sp. 'Sunbelkulave'.

Parentage:

*Female, or seed, parent*.—Proprietary selection of *Calibrachoa* sp. identified as code name CE11, not patented.

*Male, or pollen, parent*.—Proprietary selection of *Calibrachoa* sp. identified as code name CP3, not patented.

Propagation:

*Type*.—By vegetative cuttings.

*Time to initiate roots*.—About one week at 15° C. to 20° C.

*Time to produce a rooted young plant*.—About three weeks at 15° C. to 20° C.

*Root description*.—Fibrous; white in color.

*Rooting habit*.—Freely branching.

Plant description:

*Plant and growth habit*.—Trailing plant habit; freely branching habit with numerous lateral branches developing per plant; pinching enhances lateral branch development; vigorous growth habit.

*Plant height*.—About 10.4 cm.

*Plant diameter*.—About 47.2 cm.

Lateral branch description:

*Length*.—About 21.4 cm.

*Diameter*.—About 1.5 mm.

*Internode length*.—About 7 mm.

*Strength*.—Strong.

*Aspect*.—Mostly trailing.

*Texture*.—Pubescent.

*Color*.—Close to 144B.

Foliage description:

*Arrangement*.—Alternate, simple.

*Length*.—About 4.2 cm.

*Width*.—About 8 mm.

*Shape*.—Narrowly elliptic.

*Apex*.—Broadly acute.

*Base*.—Cuneate.

*Margin*.—Entire.

*Texture, upper and lower surfaces*.—Pubescent.

*Venation pattern*.—Pinnate; reticulate.

*Color*.—Developing leaves, upper surface: Close to 137C. Developing leaves, lower surface: Close to 137D. Fully expanded leaves, upper surface: Close to 137B; venation, close to 144B. Fully expanded leaves, lower surface: Close to 137C; venation, close to 144B.

*Petiole*.—Length: About 3.2 mm. Diameter: About 1.1 mm. Texture, upper and lower surfaces: Sparsely pubescent. Color, upper and lower surfaces: Close to 144B.

Flower description:

*Flower arrangement and habit*.—Single salverform flowers arising from upper leaf axils; freely flowering habit with usually about 98 flowers per plant; flowers face mostly outwardly.

*Fragrance*.—None detected.

*Natural flowering season*.—Early flowering habit, plants of the new *Calibrachoa* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Shape: Cylindrical. Length: About 2.1 cm. Diameter: About 4.7 mm. Color: Close to 85A; thin longitudinal lines, close to N92A.

*Flower diameter*.—About 3.6 cm.

*Flower length (depth)*.—About 2.3.cm.

*Throat diameter*.—About 9.5 mm.

*Tube length*.—About 1.6 cm.

*Tube diameter, base*.—About 1.8 mm.

*Corolla*.—Arrangement: Five petals fused at the base and opening into a flared trumpet. Petal length from throat: About 1.1 cm. Petal width: About 1.7 cm. Petal shape: Spatulate. Petal apex: Blunt to slightly cordate. Petal margin: Entire. Petal texture, upper and lower surfaces: Smooth, glabrous. Throat texture: Smooth, glabrous. Tube texture: Pubescent. Color: Petal, when opening, upper surface: Close to N87A; towards the throat, close to between 79A and N82A; venation, close to N92C. Petal, when opening, lower surface: Close to 84A. Petal, fully opened, upper surface: Close to N82B; towards the throat, close to between 79A and N82A; venation, close to 79A; color does not change with development. Petal, fully opened, lower surface: Close to 79D; venation, close to 79D. Throat: Close to 6A; venation, close to N187A. Tube: Close to 1C; venation, close to N199A.

*Calyx*.—Arrangement: Star-shaped calyx tube with a single whorl of five sepals fused at the base. Sepal length: About 4.5 mm to 10 mm. Sepal width: About 2.7 mm. Sepal shape: Lanceolate. Sepal apex: Acute. Sepal margin: Entire. Sepal texture, upper and lower surfaces: Pubescent. Sepal color: Immature and mature, upper surface: Close to 143C. Immature and mature, lower surface: Close to 143C.

*Peduncles*.—Length: About 2.7 cm. Diameter: About 0.8 mm. Angle: Mostly outwardly. Strength: Strong. Texture: Smooth. Color: Close to 144B.

*Reproductive organs*.—Stamens: Quantity: Five per flower. Stamen length: About 6 mm to 11 mm. Anther shape: Ellipsoidal. Anther length: About 1.5 mm. Anther diameter: About 1.3 mm. Anther color: Close to 10B. Pollen amount: Moderate. Pollen color: Close to 10B. Pistils: Quantity: One per flower. Pistil length: About 8.2 mm. Style color: Close to 145B. Stigma shape: Transversely ellipsoidal. Stigma color: Close to 144B. Ovary color: Close to 145A.

*Seed/fruit*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa* plants.

It is claimed:

1. A new and distinct *Calibrachoa* plant named 'Sunbelkulave' as illustrated and described.

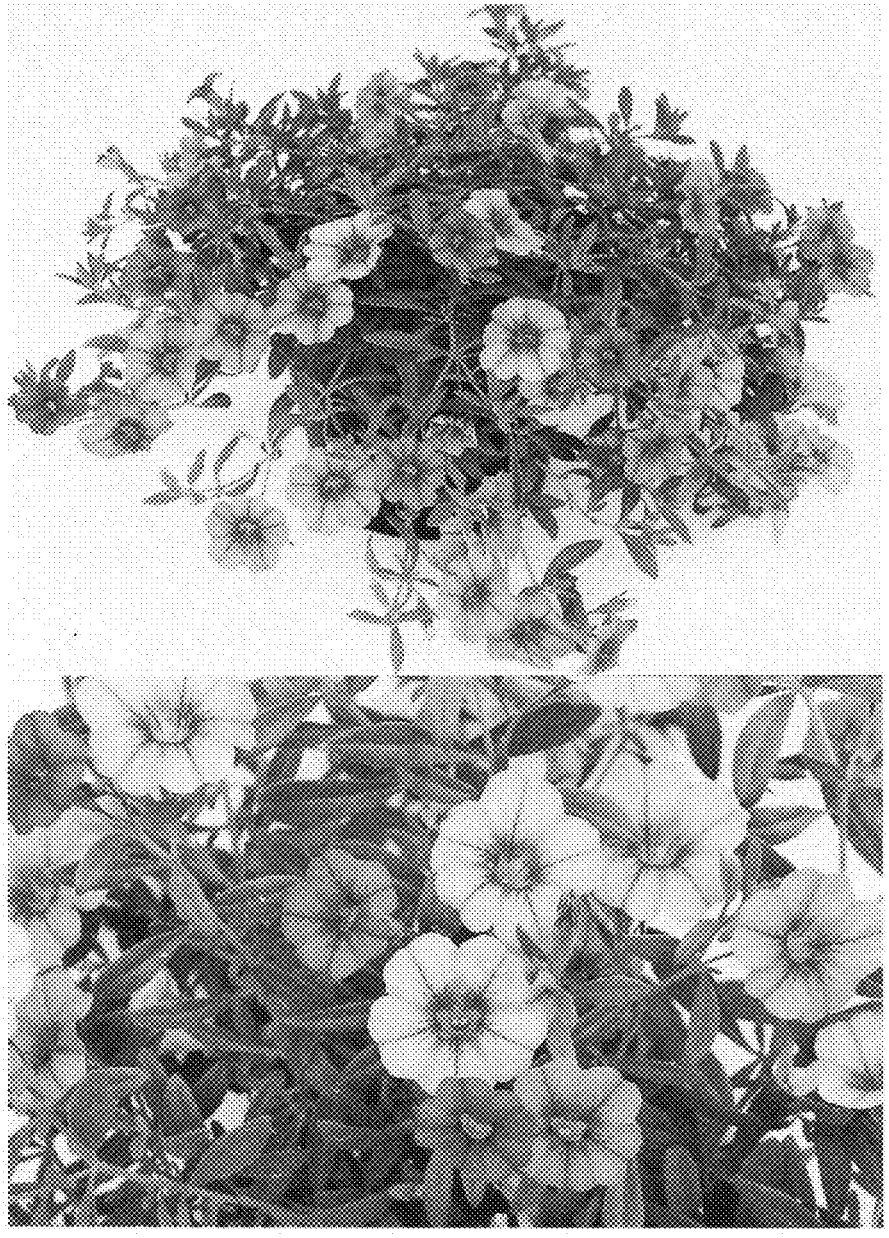

* * * * *